US00PP14650P29

(12) United States Plant Patent
Janssen

(10) Patent No.: US PP14,650 P2
(45) Date of Patent: Mar. 30, 2004

(54) BEAUCARNEA PLANT NAMED 'GOLD STAR'

(50) Latin Name: *Beaucarnea recurvata*
Varietal Denomination: Gold Star

(75) Inventor: Cornelis Johannes Janssen, Honselersdijk (NL)

(73) Assignee: Fachjan BV, Honselersdijk (NL)

( * ) Notice: Subject to any disclaimer, the term of this patent is extended or adjusted under 35 U.S.C. 154(b) by 0 days.

(21) Appl. No.: 10/408,146

(22) Filed: Apr. 6, 2003

(51) Int. Cl.[7] ..... A01H 5/00
(52) U.S. Cl. ..... Plt./373
(58) Field of Search ..... Plt./373

*Primary Examiner*—Kent Bell
(74) *Attorney, Agent, or Firm*—C. A. Whealy

(57) ABSTRACT

A distinct cultivar of Beaucarnea plant named 'Gold Star', upright and outwardly arching growth habit; dark green and yellow green variegated leaves; and excellent post-production longevity.

1 Drawing Sheet

Botanical classification/cultivar designation: *Beaucarnea recurvata* cultivar Gold Star.

BACKGROUND OF THE INVENTION

The present invention relates to a new and distinct cultivar of Beaucarnea plant, botanically known as *Beaucarnea recurvata*, and hereinafter referred to by the name 'Gold Star'.

The new cultivar was discovered by the Inventor in a greenhouse in Honselersdijk, The Netherlands as a naturally-occurring whole plant mutation of an unidentified selection of *Beaucarnea recurvata*. The new Beaucarnea was observed as a single plant in a group of plants of the parent selection in 1996. This plant was selected on its unique leaf variegation pattern as plants of the parent selection do not have variegated leaves.

Asexual propagation of the new cultivar at Enkhuizen, The Netherlands, by tissue culture since 1996 has shown that the unique features of this new Beaucarnea plant are stable and reproduced true to type in successive generations of asexual propagation.

SUMMARY OF THE INVENTION

The new Beaucarnea has not been observed under all possible environmental conditions. The phenotype may vary somewhat with variations in environment such as temperature and light intensity, without, however, any variance in genotype.

The following traits have been repeatedly observed and are determined to be the unique characteristics of 'Gold Star'. These characteristics in combination distinguish 'Gold Star' as a new and distinct cultivar:

1. Upright and outwardly arching growth habit.
2. Dark green and yellow green variegated leaves.
3. Excellent post-production longevity.

Plants of the new Beaucarnea can be compared to plants of the cultivar FACH9901BEAU, disclosed in U.S. Plant Pat. No. 12,735. In side-by-side comparisons conducted in Honselerdijk, The Netherlands, plants of the new Beaucarnea differed from plants of the cultivar FACH9901BEAU in the following characteristics:

1. Plants of the new Beaucarnea were more compact than plants of the cultivar FACH9901BEAU.
2. Plants of the new Beaucarnea had smaller and shorter leaves than plants of the cultivar FACH9901BEAU.
3. Plants of the new Beaucarnea had narrower yellow green margins than plants of the cultivar FACH9901BEAU.
4. Plants of the new Beaucarnea and the cultivar FACH9901BEAU differed in leaf coloration.

DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Beaucarnea. The photograph comprises a side perspective view of a typical plant of 'Gold Star' grown in a container.

DETAILED BOTANICAL DESCRIPTION

The aforementioned photograph and following observations and measurements describe plants grown in Honselersdijk, The Netherlands, in a glass-covered greenhouse with day temperatures about 14 to 32° C. and night temperatures about 7 to 16° C. Plants were about two years from planting and were grown in 15-cm containers. In this description, color references are made to The Royal Horticultural Society Colour Chart, 1995 Edition, except where general terms of ordinary dictionary significance are used.

Botanical classification: *Beaucarnea recurvata* cultivar Gold Star.

Parentage: Naturally-occurring whole plant mutation of an unidentified selection of *Beaucarnea recurvata*, not patented.

Propagation:

*Method.*—By tissue culture.

*Time to initiate roots on a tissue-cultured plantlet.*—About 70 to 84 days at 23 to 24° C.

*Time to produce a root tissue-cultured plant.*—About 120 to 150 days at 23 to 24° C.

*Root description.*—Fine.

Plant description:

*Plant shape.*—Upright plant habit with outwardly arching leaves; symmetrical; moderately vigorous growth habit.

*Plant height from soil level to top of leaf plane.*—About 40 cm.

*Plant diameter or spread.*—About 65 cm.

*Foliage description.*—Arrangement: Single; rosette. Length: About 59 cm. Width: About 9.5 mm. Shape: Linear. Apex: Acute, elongated. Attachment: Decurrent. Margin: Very fine serrations. Aspect: Initially upright, then outwardly arching. Texture, upper and lower surfaces: Leathery, smooth, glabrous. Venation pattern: Parallel. Color: Longitudinally variegated. Marginal areas are golden to lemon yellow and the central area is dark green. On the largest leaves, the marginal areas are each about 1.5 mm wide. Developing leaves, upper surface: Central area: Towards base, 145B; mid-section and apex, 137A. Marginal areas: Towards base, 145C; mid-section and apex, 150C. Developing leaves, lower surface: Central area: Towards base, 145A to 145B; mid-section and apex, between 139A and 137A. Marginal areas: Towards base, 145C; mid-section and apex, 150C. Fully expanded leaves, upper and lower surfaces: Central area: Between 139A and 137A. Marginal areas: 144A. Venation, upper and lower surfaces: Same as lamina.

Flower description: Flower development has not been observed on plants of the new Beaucarnea.

Disease/pest resistance: Plants of the new Beaucarnea have not been observed to be resistant to pathogens and pests common to Beaucarnea.

Postproduction longevity: Plants of the new Beaucarnea have been observed to maintain good leaf substance for more than two years in an interior environment.

Weather tolerance: Plants of the new Beaucarnea have been observed to be tolerant to temperatures ranging from 10 to at least 40° C.

It is claimed:

1. A new and distinct cultivar of Beaucarnea plant named 'Gold Star' as illustrated and described.

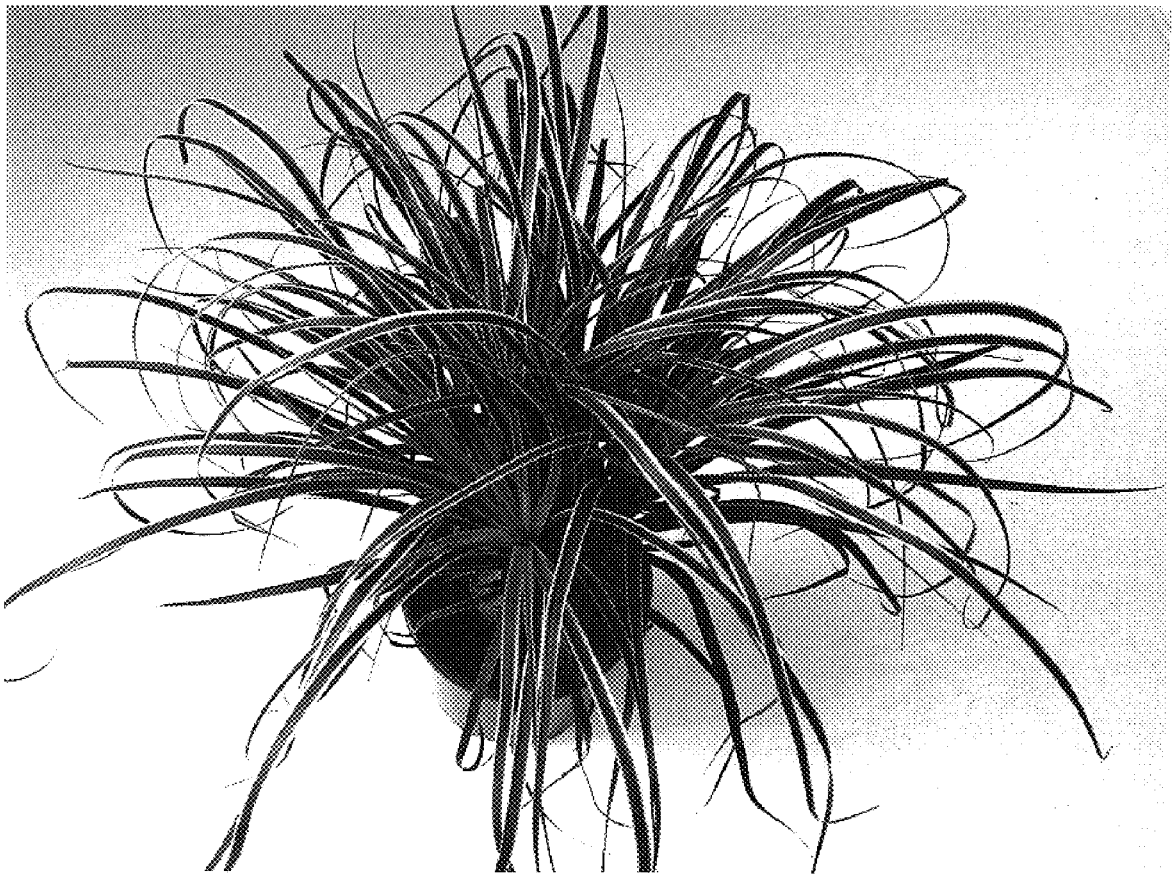

* * * * *